United States Patent [19]

Berglund et al.

[11] Patent Number: 5,201,705
[45] Date of Patent: Apr. 13, 1993

[54] DEVICE FOR RELEASE OF A SUBSTANCE

[75] Inventors: Bengt G. Berglund, Göteborg; Billy N. Nilson, Mjölby; Åke S. Nilsson, Göteborg, all of Sweden

[73] Assignee: Aktiebolaget Hassle, Sodertalje, Sweden

[21] Appl. No.: 520,129

[22] PCT Filed: Jul. 6, 1987

[86] PCT No.: PCT/SE87/00319
§ 371 Date: Feb. 14, 1989
§ 102(e) Date: Feb. 14, 1989

[87] PCT Pub. No.: WO88/00476
PCT Pub. Date: Jan. 28, 1988

Related U.S. Application Data

[63] Continuation of Ser. No. 297,245, Feb. 14, 1989, abandoned.

[30] Foreign Application Priority Data

Jul. 10, 1986 [SE] Sweden .................... 8603072

[51] Int. Cl.[5] ............... A61M 31/00; A61M 37/00; E03B 11/00
[52] U.S. Cl. ........................ 604/56; 604/85; 604/92; 137/268
[58] Field of Search ............. 137/268, 345; 251/125, 251/625.46; 604/56, 82-86, 246, 248, 251, 252, 416, 89-92

[56] References Cited

U.S. PATENT DOCUMENTS

| | | | |
|---|---|---|---|
| 2,345,275 | 3/1944 | Marvin | 604/85 |
| 3,003,518 | 10/1961 | Tisdale | 137/268 |
| 3,051,174 | 8/1962 | Mandell | 604/84 |
| 4,465,471 | 8/1984 | Harris et al. | 604/56 |
| 4,474,574 | 10/1984 | Wolfe et al. | 604/85 |
| 4,534,758 | 8/1985 | Akers et al. | 604/85 |
| 4,581,014 | 4/1986 | Millerd et al. | 604/80 |
| 4,671,311 | 6/1987 | Hepperle et al. | 137/268 |
| 5,005,604 | 4/1991 | Aslanian | 137/556 |

FOREIGN PATENT DOCUMENTS 0275821 8/1927 United Kingdom ............... 604/84

Primary Examiner—John D. Yasko
Assistant Examiner—Adam J. Cormak
Attorney, Agent, or Firm—White & Case

[57] ABSTRACT

A device for release of a solid substance into a flowing liquid during parenteral administration of the liquid to a patient includes a connector (1, with an inlet (6) and an outlet (12) for the liquid, and a valve assembly (4,5). The valve assembly has a valve core (5) which is rotatable between a bypass position and a working position. A releasable container (15), containing the solid substance, may be connected to the valve core (5). In the bypass position, liquid is conducted from the inlet to the outlet, by-passing the container (15). When the valve core (5) is moved to the working position, liquid is diverted into the container (15), for mixing with the solid substance, and then returned to the connector, where it then exits through the outlet (12).

10 Claims, 3 Drawing Sheets

DEVICE FOR RELEASE OF A SUBSTANCE

This application is a continuation of application Ser. No. 297,245, filed on Feb. 14, 1989, now abandoned.

The present invention is related to a device intended to be used in parenteral liquid administration to a patient, whereby one during such administration desires to release a substance, such as a drug, to the liquid.

A device by which drugs can be supplied to a parenteral liquid flow is shown by EP-B-0059694. Modified such devices are shown by EP-A-0077604, EP 85850141.4, EP-A-0100296 and WO 86/03416. A device for connection into a flow of infusion liquid, where the liquid by means of a valve can be led either via a vial for a drug to the patient or bypassing said vial, is shown by EP-A-0163387. A similar device having three operative valve positions, one for bypass of the liquid, one for dilution of a drug and one for emptying of a drug solution in an administration system, is shown by U.S. Pat. No. 4,534,758. The two lastmentioned systems require that a liquid preparation ready for administration is formed in the vial before the valve is put in an administration position.

An object of the present invention is to achieve a device where a container for a dry drug preparation exchangeably can be connected to a liquid administration system, whereupon the liquid can be deviated and brought into contact with the drug thus that the drug is added to the liquid during administration of the liquid. A further object is to achieve a device where inadvertent deviation of the liquid is avoided when no drug container is connected.

Thus the device of the invention is a device for release of a substance from a solid preparation thereof to a flowing liquid during simultaneous parenteral administration of the liquid to a patient, which device comprises a connector connectable into a system for parenteral administration of the liquid, and having an inlet and outlet with a valve device which comprises a mobile valve core having a bypass position providing for direct liquid flow from the inlet to the outlet of the connector and a working position providing for liquid flow from the inlet of the connector into a releasable container for the solid preparation. The device of an invention is characterized in that the valve core has an outlet means and a separate inlet means simultaneously connectable to an inlet means and a separate outlet means respectively on the releasable container, the releasable container further having therein means for conducting the liquid from the inlet thereof to a space where it will contact the solid preparation, and further to the outlet of the releasable container, and via the valve core in a flow path to the outlet of the connector.

In a preferred embodiment of the invention the releasable container is a manoeuvre device for the valve core and the valve core has no other manoeuvre devices. Thus, when the valve core is rotatable in the valve device the releasable container may function as a handle gripping the end of the valve core by means of its inlet and outlet means. Inadvertent deviation of the liquid when no container is connected will be avoided by the invention in particular by this embodiment. Thus risks of liquid spillage and air suction into the administration system are reduced.

Preferably the outlet and inlet of the valve core are connectable to the inlet and outlet of the releasable container by socket means, and preferably the socket means are tapered sockets fitting in tapered holes, and preferably the tapered sockets are the outlet means and inlet means of the releasable container and that the tapered holes are the inlet means and outlet means on the valve core.

In a specially preferred embodiment of the device a filter is arranged within the connector in the flow path from the valve in the working position to the outlet of the connector. Suitably the flow of liquid in the bypass position of the valve has dual flow paths to the outlet either through the filter or via the valve core.

Use of a device as described for release of a substance from a solid preparation thereof to a liquid during simultaneous parenteral administration ministration of the liquid to a patient is a further embodiment of the invention.

The invention is further described with the reference to the enclosed drawings where FIG. 1 shows a device according to the invention in a bypass position.

Figures 1, 2:
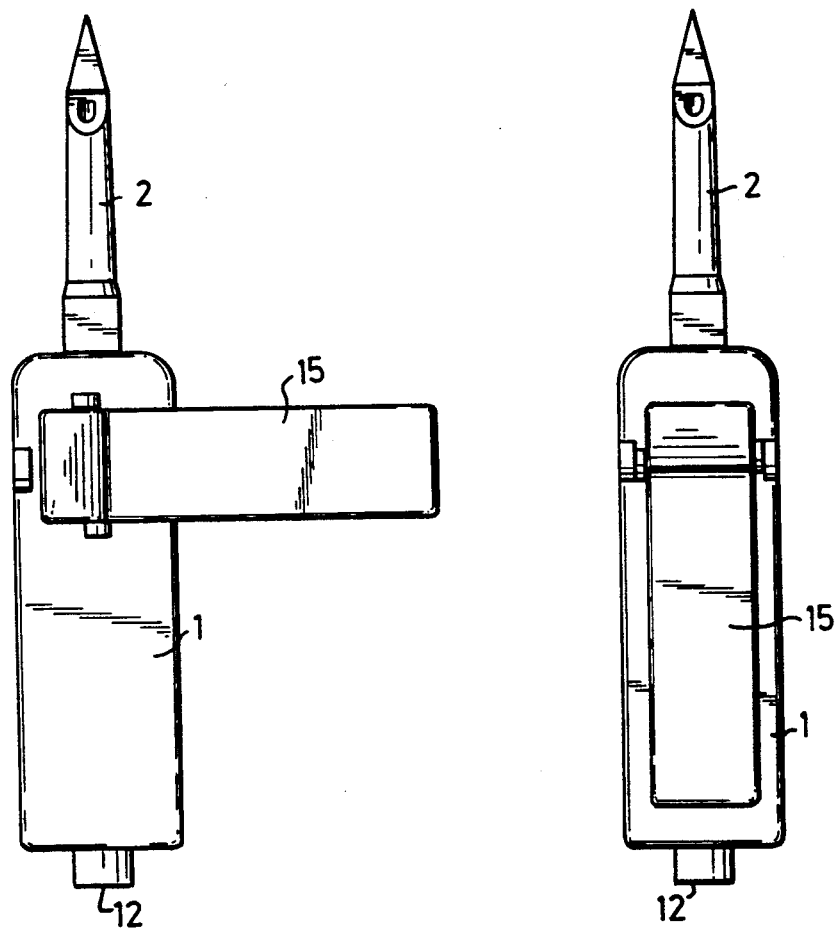
FIG. 2 shows the device in FIG. 1 in a working position.
Figure 3:
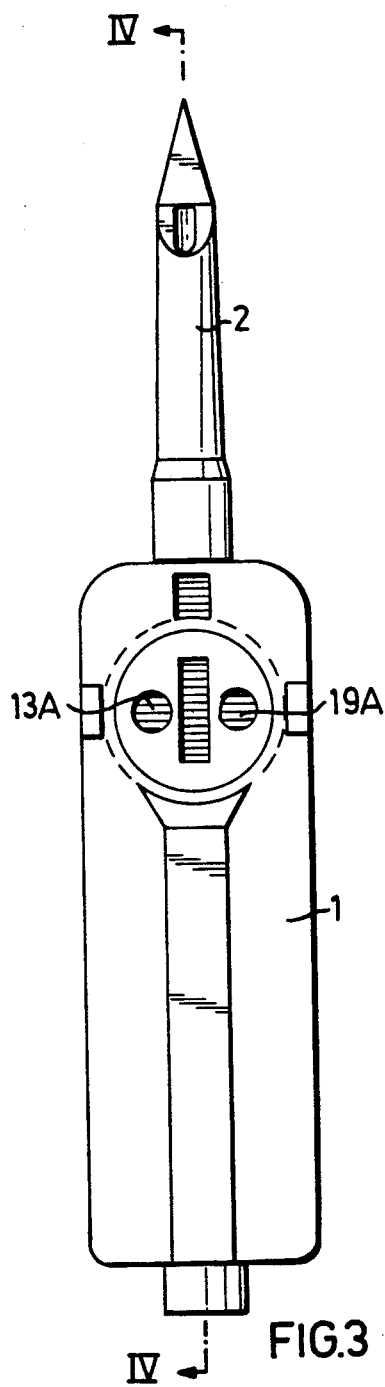
FIG. 3 shows a connector in a bypass position.
Figure 4:
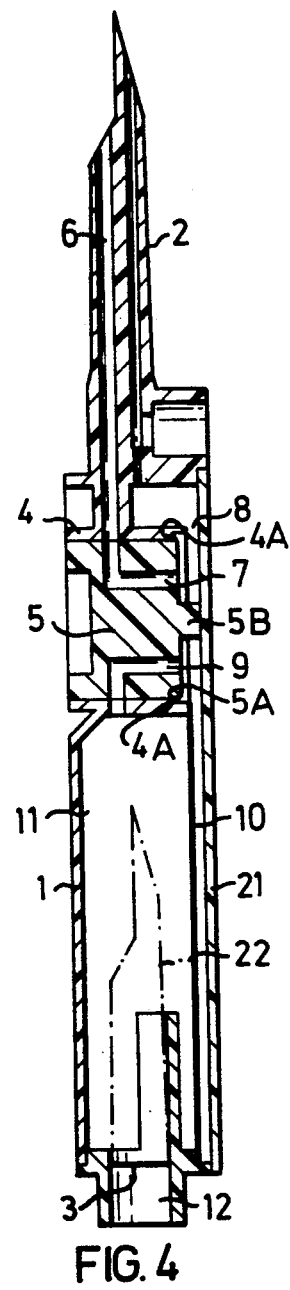
FIG. 4 shows a connector in a bypass position in section along the line IV—IV in FIG. 3.

With 1 is denoted a connector having an inlet via a transfer cannula 2 in one end thereof, that will usually be the upper end in use, and an outlet via a piercable membrane 3 in the opposite end thereof. In the connector there is a valve device consisting of a cylindrical valve housing 4 and a cylindrical valve core 5 turnable therein. Through the transfer cannula 2 an inlet channel 6 runs, which in the bypass position of the valve shown in FIG. 4 opens into a first bypass channel 7 through the valve core, said bypass channel opening into a first inner space 8 in the connector. From the first inner space the liquid may, when the valve is in the bypass position, follow either of dual flow paths via a second bypass channel 9 through the valve core or via a bacteria filter 10, sealingly attached along its periphery to walls defining a second inner space 11 in the connector, to said second inner space which can be put in liquid connection with the outlet 12 of the connector via the membrane 3.

Figures 5, 6:
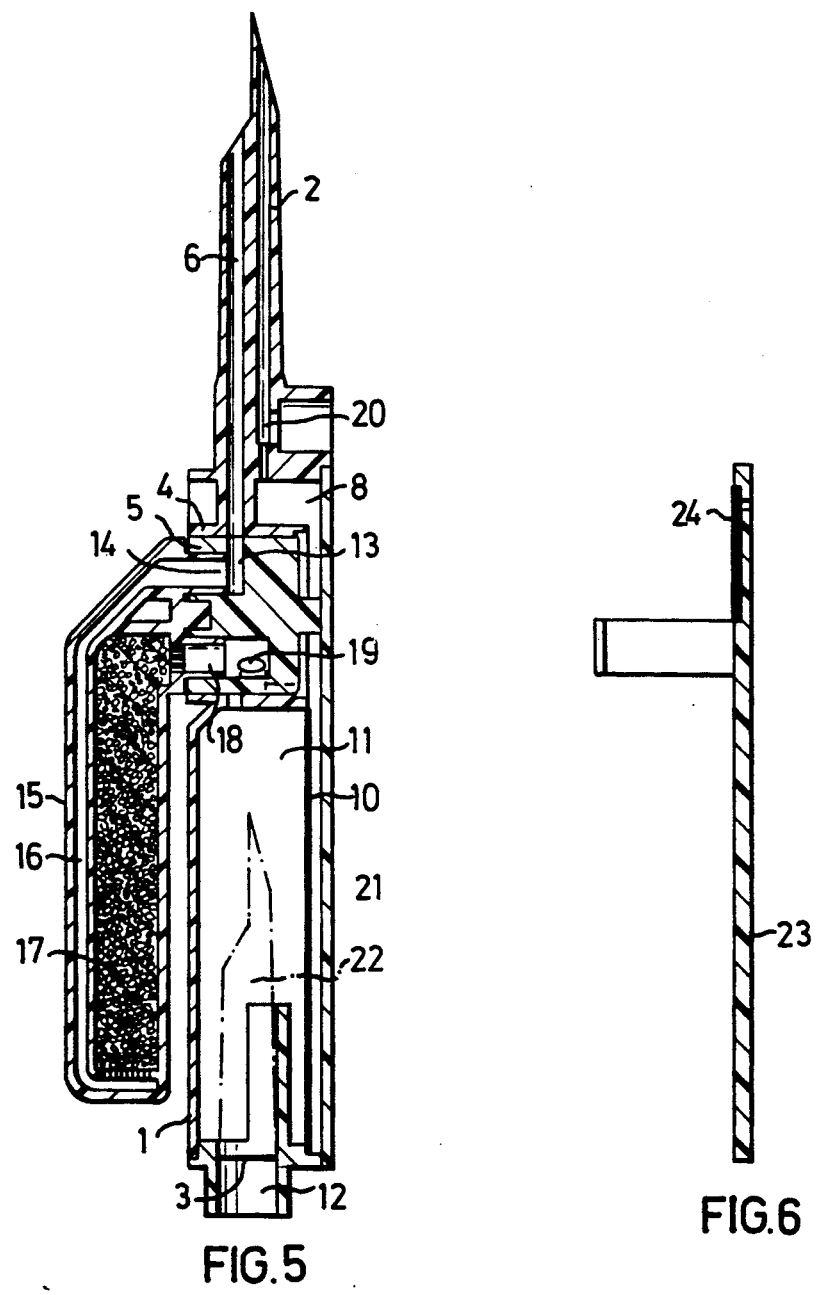
FIG. 5 shows a section through a connector in a working position, with a container for a drug.
FIG. 6 shows an alternative rear portion of the connector in FIGS. 1-5.

In the working position of the valve as shown in FIG. 5, which position is at a 90° angle with the bypass position, the inlet channel 6 opens into a channel 13 through the valve core, which channel via an outlet means of the valve core being a tapered opening 13A is in communication therein with tapered inlet socket 14 on a releasable drug container 15 being shaped substantially like an elongated box having its inlet socket 14 and a separate tapered outlet socket 18 adjacent to each other extending from one of the elongated faces thereof adjacent to one end thereof. Via an inlet channel 16 and a bed of granules 17 of the pharmaceutical preparation of the drug being released to the liquid, the liquid may circulate to the outlet socket 18 of the container, which socket via a tapered opening 19A in the valve core, being inlet means thereof, is in communication with a channel 19 through the valve core. Said channel opens into the first inner space 8, while the channel 19 has no opening directly into the second inner space 11, whereby the liquid at the working position of the valve can only pass via filter 10 to space 11. The cylindrical surface of the valve core 5 seals against the cylindrical surface of the valve housing 4. The valve core is secured against axial movement by a flange 5A thereon resting against an edge 4A in the valve housing and by an axial extension 5B to the valve core resting against a rear wall 21 of the connector 1. An airing channel 20 is in a manner known per se arranged through the transfer cannula 2. The first inner space 8 is limited by the rear portion 21 of the chamber and by side and end walls of the connector 1 and by the filter 10. A second transfer cannula for connection of a drip chamber via the membrane 3 to the connector is hinted with 22. Alternatively a drip chamber function may be built into the connector 1 or located at a different position in the system.

An alternative rear portion 23 has a hydrophobic filter 24 through which air from the downstream parts of the administration system can be let out.

While the device of the invention has a bypass position of the valve thereof and a working position in which the substance is released and administered it does not have a position in which the substance is merely reconstituted or dissolved while remaining in the releasable container.

The parenteral administration system may further comprise known details such as a liquid container (bottle or gag), conduits, injection ports, branchings, clasps, pumps, a cannula etc.

The device may be made as molded plastic parts, preferably in disposable design.

We claim:

1. A device for release of a solid preparation into a flowing liquid during simultaneous parenteral administration of the liquid to a patient, the device comprising a connector having:
    an inlet and an outlet connectable into a system for parental administration of a liquid; and
    a valve means in fluid communication with the inlet; wherein the valve means includes a valve housing, a valve core rotatable in the valve housing between a bypass position and a working position; wherein the valve core has an outer coupling surface containing an external outlet port and an external inlet port spaced from the outlet port for connection to a releasable container; wherein the valve means further includes first passage means for directing fluids from the connector inlet to the connector outlet when the valve core is in the bypass position; and wherein the valve means includes second passage means for directing fluids from the connector inlet to the external outlet port, and third passage means for directing fluids from the external inlet port to the connector outlet, when the valve core is in the working position, wherein the connector includes first and second flow paths between the valve core and the connector outlet; wherein the first flow path is essentially unrestricted; wherein the second flow path includes a filter means; wherein the first passage means communicates with the first flow path when the valve core is in the bypass position; and wherein the third passage means communicates only with the second flow path when the valve core is in the working position.

2. A device according to claim 1, wherein the valve core includes a rotational axis, and the ports extend parallel to the rotational axis and are disposed on opposite sides thereof.

3. A device for release of a solid preparation into a flowing liquid during simultaneous parenteral administration of the liquid to a patient, comprising a connector and a releasable container, wherein the connector comprises:
    an inlet and an outlet connectable into a system for parental administration of a liquid; and a valve means in fluid communication with the inlet; wherein the valve means includes a valve core moveable between a bypass position and a working position; wherein the valve core has an external outlet port and an external inlet port spaced from the outlet port for connection to a releasable container; wherein the valve means includes first passage means for directing fluids from the connector inlet to the connector outlet when the valve core is in the bypass position; and wherein the valve means includes second passage means for directing fluids from the connector inlet to the external outlet port, and third passage means for directing fluids from the external inlet port to the connector outlet, when the valve core is in the working position; and
    wherein the releasable container includes a space for containing a solid preparation, a container inlet and a separate container outlet; means for releasably coupling the container inlet and outlet to the valve core outlet port and valve core inlet port, respectively; and container passage means for directing fluid from the container inlet to flow into the space and to exit the space at a distance therefrom to the container outlet.

4. A device according to claim 3, wherein the releasable container is a maneuverable device for the valve core and that the valve core has no other maneuverable devices.

5. A device according to claim 4, wherein the means for coupling the container and valve core comprise socket means.

6. A device according to claim 5, wherein the socket means comprise tapered holes and tapered sockets fitting therein.

7. A device according to claim 6, wherein the tapered sockets are disposed on the releasable container and that the tapered holes are provided in the valve core.

8. A device according to claim 3, wherein the container passage means is arranged such that liquid enters and exits the space substantially at opposite ends thereof.

9. A device according to claim 3, wherein the connector includes first and second flow paths between the valve core and the connector outlet; where in the first flow path is essentially unrestricted; wherein the second flow path includes a filter means; wherein the first passage means communicates with the second flow path when the valve core is in the bypass position; and wherein the third passage means communicates only with the second flow path when the valve core is in the working position.

10. A method of dispensing a solid preparation comprising the steps of:
    (a) providing a connector having an inlet, an outlet, and valve means in fluid communication with the inlet; wherein the valve means includes a valve core moveable between a bypass position and a working position; wherein the valve core has an external outlet port and an external inlet port spaced from the outlet port for connection to a releasable container; wherein the valve means includes first passage means for directing fluids from the connector inlet to the connector outlet when the valve core is in the bypass position; and wherein the valve means includes second passage means for directing fluids from the connector inlet to the external outlet port, and third passage means for directing fluids from the external inlet port to the connector outlet, when the valve core is in the working position;

(b) positioning the valve core into the bypass position;

(c) connecting the inlet and outlet into a parental administration tube containing a liquid so that liquid flows through the connector;

(d) providing a releasable container which includes a space for containing a solid preparation, a container inlet and a separate container outlet; means for releasable coupling the container inlet and outlet to the valve core outlet port and valve core inlet port, respectively; and passage means for directing fluid from the container inlet to flow into the space and to exit the space as a distance therefrom to the container outlet;

(e) coupling the releasable container to the connector; and (f) moving the valve core from the bypass position to the working position such that the liquid in the parental administration tube is diverted through the space containing the preparation thereby dispensing the same.

* * * * *

UNITED STATES PATENT AND TRADEMARK OFFICE
CERTIFICATE OF CORRECTION

PATENT NO. : 5,201,705
DATED : April 13, 1993
INVENTOR(S) : Berglund et al.

It is certified that error appears in the above-indentified patent and that said Letters Patent is hereby corrected as shown below:

In the abstract, line 3, after "(1," insert --)--;

col. 2, line 14, delete "ministration;"

col. 3, line 27, change "gag" to --bag--;

col. 4, line 63, after "and" insert --a--;

col. 6, line 8, change "as" to --at--.

Signed and Sealed this

Third Day of February, 1998

*Attest:*

BRUCE LEHMAN

*Attesting Officer*   *Commissioner of Patents and Trademarks*